United States Patent [19]

Seele et al.

[11] Patent Number: 5,017,595
[45] Date of Patent: May 21, 1991

[54] AZOLYLMETHYLALLYL ALCOHOLS AND FUNGICIDES CONTAINING THESE COMPOUNDS

[75] Inventors: Rainer Seele, Fussgoenheim; Hubert Sauter, Mannheim; Reiner Kober, Fussgoenheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 318,954

[22] Filed: Mar. 6, 1989

[51] Int. Cl.$^5$ .................. A01N 43/653; C07D 249/08
[52] U.S. Cl. ..................... 514/383; 514/184; 548/101; 548/267.8
[58] Field of Search ............ 548/101, 262, 101, 267.8, 548/268.6; 514/184, 383

[56] References Cited

U.S. PATENT DOCUMENTS

| | | | |
|---|---|---|---|
| 4,634,466 | 1/1987 | Noon et al. | 514/383 |
| 4,655,820 | 4/1987 | Worthington et al. | 548/262 |
| 4,719,307 | 1/1988 | Lantzsch et al. | 548/262 |
| 4,723,984 | 2/1988 | Holmwood et al. | 548/262 |

FOREIGN PATENT DOCUMENTS 0052424 5/1982 European Pat. Off. .

Primary Examiner—Mary C. Lee
Assistant Examiner—Patricia L. Morris
Attorney, Agent, or Firm—Oblon, Spivak, McClelland, Maier & Neustadt

[57] ABSTRACT

Azolylmethylallyl alcohols of the formula I

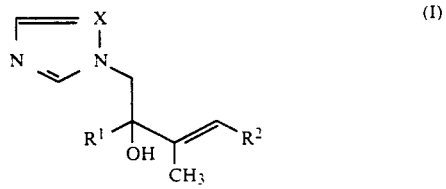

where $R_1$ and $R_2$ are alkyl, naphthyl, biphenyl, cycloalkyl, cycloalkenyl or phenyl, these radicals being unsubstituted or substituted, X is CH or N, their plant-tolerated acid addition salts and metal complexes. and fungicides containing these compounds.

6 Claims, No Drawings

AZOLYLMETHYLALLYL ALCOHOLS AND FUNGICIDES CONTAINING THESE COMPOUNDS

The present invention relates to novel azole compounds, processes for their preparation and fungicides containing these compounds.

It is known that triazolylbutenol derivatives, for example 1-(1,2,4-triazol-1-ylmethyl)-1-(4-chlorophenyl)-3-(2-chlorophenyl)-prop-2-en-1-ol, can be used as fungicides (EP-52 424). However, its fungicidal action is insufficient.

We have found that azolylmethylallyl alcohols of the general formula I

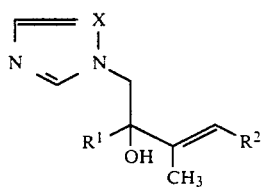

where $R^1$ and $R^2$ are identical or different and are each $C_1$–$C_4$-alkyl, naphthyl, biphenyl, $C_3$–$C_{12}$-cycloalkyl, cycloalkenyl or phenyl, these radicals being unsubstituted or monosubstituted to trisubstituted by halogen, nitro, phenoxy, alkyl, alkoxy, amino or haloalkyl of 1 to 4 carbon atoms, and X is CH or N, and their plant-tolerated acid addition salts and metal complexes have a bet-ter fungicidal action, in particular against cereal diseases, than the known azole compound.

The compounds of the formula I are generally obtained in the form of racemates having an E configuration at the C=C double bond. The racemates can be separated by known methods, for example via diastereomeric esters of optically pure acids, and can be isolated in pure form. Both the pure enantiomers and their racemates obtained in the synthesis can be used as fungicides. The present invention embraces all these compounds.

$R^1$ and $R^2$ are each, for example, methyl, ethyl, isopropyl, n-propyl, n-butyl, sec-butyl, tert-butyl, phenyl, halophenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, alkoxyphenyl, 2-methoxyphenyl, 3-methoxyphenyl, 4-methoxyphenyl, 2,4-dimethoxyphenyl, alkylphenyl, 4-ethylphenyl, 4-isopropylphenyl, 4-tert-butylphenyl, 4-tertbutoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, cyclopropyl, cyclobutyl, cyclopentyl, cyclohexyl, cyclooctyl, cyclododecyl, 2-cyclohexenyl, 3-cyclohexenyl, naphthyl or biphenyl.

Acid addition salts are, for example, the salts with inorganic or organic acids, for example the hydrochlorides, bromides, sulfates, nitrates, phosphates, oxalates or dodecylbenzenesulfonates. The activity of the salts is due to the cation, so that in general any anion may be chosen. The novel active ingredient salts are prepared by reacting the azolylmethyloxiranes with the acids.

Metal complexes of the active ingredients I or their salts can be formed, for example, with the metals copper, zinc, tin, manganese, iron, cobalt or nickel, by reacting the azolylmethylallyl alcohols with the metal salts, for example with copper sulfate, tin chloride or zinc sulfate.

The compounds of the formula I can be prepared, for example, by reacting a compound of the formula II

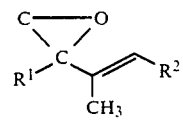

where $R^1$ and $R^2$ have the abovementioned meanings, with a compound of the formula III

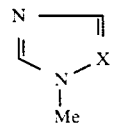

where Me is hydrogen or a metal atom (Na or K) and X has the stated meanings.

Where Me is hydrogen, the reaction is carried out in the presence or absence of a solvent or diluent and with or without the addition of an inorganic or organic base and of a reaction accelerator, at from 10° to 120° C. The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane or mixtures of these.

Examples of suitable bases, which may also be used as acid acceptors in the reaction, are alkali metal hydroxides, such as lithium hydroxide, sodium hydroxide or potassium hydroxide, alkali metal carbonates, such as sodium carbonate, potassium carbonate or cesium carbonate, or sodium bicarbonate, potassium bicarbonate or cesium bicarbonate, pyridine or 4-dimethylaminopyridine. However, it is also possible to use other conventional bases.

Preferred reaction accelerators are metal halides, such as sodium iodide or potassium iodide, quaternary ammonium salts, such as tetrabutylammonium chloride, bromide, iodide or bisulfate or benzyltriethylammonium chloride or bromide or crown ethers, such as 12-crown-4, 15-crown-5, 18-crown-6, dibenzo-18-crown-6 or dicyclohexano-18-crown-6.

The reaction is carried out in general at from 20° to 150° C., under atmospheric or superatmospheric pressure, continuously or batchwise.

Where Me is a metal atom, reaction (a) is carried out in the presence or absence of a solvent or diluent and with or without the addition of a strong inorganic or organic base, at from −10° to 120° C. The preferred solvents and diluents include amides, such as dimethylformamide, diethylformamide, dimethylacetamide, diethylacetamide, N-methylpyrrolidone or hexamethylphosphorotriamide, and sulfoxides, such as dimethyl sulfoxide or sulfolane.

Examples of suitable bases, which may also be used as acid acceptors in the reaction, are alkali metal hydrides, such as lithium hydride, sodium hydride and potassium hydride, alkali metal amides, such as sodium amide and potassium amide, and sodium tert-butoxide, potassium tert-butoxide, triphenylmethyllithium, trimethylsodium, triphenylmethylpotassium, naphthalenelithium, naphthalenesodium and naphthalenepotassium.

Suitable diluents for reaction (b) are polar organic solvents, such as nitriles, e.g. acetonitrile, sulfoxides, e.g. dimethyl sulfoxide, formamides, e.g. dimethylformamide, ketones, e.g. acetone, ethers, e.g. diethyl ether or tetrahydrofuran, and in particular chlorohydrocarbons, e.g. methylene chloride and chloroform.

The reaction is carried out in general at from 0° to 100° C., preferably from 20° to 80° C. When a solvent is present, the reaction is advantageously carried out at the boiling point of the particular solvent.

The novel starting compounds II can be prepared by known methods, in a simple manner, from the unsaturated ketones of the formula IV

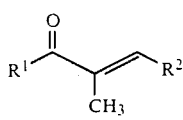

IV (cf. Corey and Chaykovsky, J. Amer. Chem. Soc. 64 (1962), (3782).

The compounds IV can be prepared by generally known methods for olefin synthesis (Houben-Weyl-Müller, Methoden der organischen Chemie, Georg Thieme Verlag, Stuttgart, 1972, Vol. V, 1 b).

The Examples which follow illustrate the preparation of the active ingredients.

I. Preparation of the starting materials

[EXAMPLE A]

5.85 g of sodium hydroxide in 40 ml of water are added to a solution of 50 g of 2-chlorobenzaldehyde in 200 ml of ethanol. The reaction mixture is cooled to 10° C. and 60 g of 4-chloropropiophenone are added, the temperature of the solution increasing to 30°-40° C. Stirring is carried out for 10 hours at 50° C., after which 200 ml of water are added to the reaction solution and the resulting emulsion is extracted by shaking with methyl tert-butyl ether. The organic phase is separated off, dried over sodium sulfate and evaporated down under reduced pressure from a water pump. In the subsequent distillation of the remaining residue, 84 g (80%) of 4-chlorophenyl β-methyl-2-chlorophenylstyryl ketone pass over under 0.25 mbar and at 127° C., and the product can be crystallized from methyl tert-butyl ether/n-hexane. Mp.: 45°-47° C.

[EXAMPLE B]

54 g of trimethylsulfonium methylsulfate and 120 ml of sodium hydroxide solution (50% strength by weight) are added to a solution of 84 g of 4-chlorophenyl β-methyl-2-chlorophenylstyryl ketone in 300 ml of methylene chloride. The reaction mixture is stirred for 12-15 hours at room temperature (20° C.), after which 300 ml of water are added to the solution and the organic phase is separated off. The organic phase isolated is washed twice with water, dried over sodium sulfate and evaporated down, 73 g (83%) of 2-(4-chlorophenyl)-2-(1-methyl-2-[2-chlorophenyl]-ethenyl)-oxirane being obtained.

II. Preparation of the end products

[EXAMPLE 1]

12 g of sodium hydroxide are added to a solution of 70 g of triazole in 300 ml of N-methylpyrrolidone and the mixture is heated for 30 minutes at 50° C. Thereafter, 73 g of 2-(4-chlorophenyl)-2-(1-methyl-2-[2-chlorophenyl]-ethenyl)-oxirane, dissolved in 100 ml of N-methylpyrrolidone, are slowly added dropwise at room temperature. The reaction mixture is stirred for 15 hours at room temperature after which 300 ml of water are added to the solution and the mixture is extracted several times by shaking with methyl tert-butyl ether. The organic phase isolated is washed twice with water and then dried over sodium sulfate and evaporated down. Crystallization of the residue from methyl tert-butyl ether/n-hexane gives 85 g (95%) of 1-(1,2,4-triazol-1-ylmethyl)-1-(4-chlorophenyl)-2-methyl-3-(2-chlorophenyl)-propenol of melting point 141°-143° C.

The compounds listed in the Table can be prepared similarly to Example 1.

TABLE

| Example | R$_1$ | R$_2$ | X | M.p./IR (°C.) |
|---|---|---|---|---|
| 1 | 4-Cl—C$_6$H$_4$ | 2-Cl—C$_6$H$_4$ | N | 141-143 |
| 2 | 4-Cl—C$_6$H$_4$ | 2-Cl—C$_6$H$_4$ | CH | |
| 3 | phenyl | 3-Cl—C$_6$H$_4$ | N | |
| 4 | phenyl | 3-Cl—C$_6$H$_4$ | CH | |
| 5 | phenyl | 4-Cl—C$_6$H$_4$ | N | |
| 6 | phenyl | 4-Cl—C$_6$H$_4$ | CH | |
| 7 | phenyl | 2,4-Cl$_2$—C$_6$H$_3$ | N | 153-157 |
| 8 | phenyl | 2,4-Cl$_2$—C$_6$H$_3$ | CH | |
| 9 | phenyl | 2-F—C$_6$H$_4$ | N | 162-164 |
| 10 | phenyl | 2-F—C$_6$H$_4$ | CH | 182-184 |
| 11 | phenyl | 4-F—C$_6$H$_4$ | N | 145-147 |
| 12 | phenyl | 4-F—C$_6$H$_4$ | CH | 164-166 |
| 13 | phenyl | 2-Cl-4-F—C$_6$H$_3$ | N | |

TABLE-continued $$\text{structure with imidazole/triazole ring, N-CH}_2\text{-C(OH)(R}^1\text{)-C(CH}_3\text{)=CH-R}^2$$

| Example | R₁ | R₂ | X | M.p./IR (°C.) |
|---|---|---|---|---|
| 14 | phenyl | 2-Cl-4-F—C₆H₃ | CH | |
| 15 | phenyl | 3-NO₂—C₆H₄ | N | |
| 16 | phenyl | 4-NO₂—C₆H₄ | N | |
| 17 | phenyl | 3-NH₂—C₆H₄ | N | |
| 18 | phenyl | 4-NH₂—C₆H₄ | N | |
| 19 | phenyl | 2-OCH₃—C₆H₄ | N | |
| 20 | phenyl | 4-OCH₃—C₆H₄ | N | |
| 21 | phenyl | 4-tert.butyl-C₆H₄ | N | |
| 22 | phenyl | cyclohexyl | N | |
| 23 | phenyl | cyclohexyl | CH | |
| 24 | phenyl | cyclohexenyl | N | |
| 25 | phenyl | cyclohexenyl | CH | |
| 26 | phenyl | cyclopentyl | CH | |
| 27 | phenyl | cyclopentyl | N | |
| 28 | phenyl | cyclopropyl | CH | |
| 29 | phenyl | phenyl | N | 168–170 |
| 30 | phenyl | norbornyl | N | |
| 31 | phenyl | norbornyl | CH | |
| 32 | phenyl | 2-Cl—C₆H₄ | N | 130–132 |
| 33 | phenyl | 2-Cl—C₆H₄ | CH | 155–157 |
| 34 | 4-Cl—C₆H₄ | 4-Cl—C₆H₄ | N | 1490, 1276, 1092, 1014, 831 cm⁻¹ |
| 35 | 4-Cl—C₆H₄ | 4-Cl—C₆H₄ | CH | |
| 36 | 4-Cl—C₆H₄ | 3-Cl—C₆H₄ | N | |
| 37 | 4-Cl—C₆H₄ | 3-Cl—C₆H₄ | CH | |
| 38 | 4-Cl—C₆H₄ | 2,4-Cl₂—C₆H₃ | N | 164–166 |
| 39 | 4-Cl—C₆H₄ | 2,4-Cl₂—C₆H₃ | CH | 1469, 1276, 1087, 860 cm⁻¹ |
| 40 | 4-Cl—C₆H₄ | phenyl | N | |
| 41 | 4-Cl—C₆H₄ | phenyl | CH | |
| 42 | 4-Cl—C₆H₄ | 2-F—C₆H₄ | N | |
| 43 | 4-Cl—C₆H₄ | 2-F—C₆H₄ | CH | |
| 44 | 4-Cl—C₆H₄ | 4-F—C₆H₄ | N | resin |
| 45 | 4-Cl—C₆H₄ | 4-F—C₆H₄ | CH | 174–176° C. |
| 46 | 4-Cl—C₆H₄ | 3-NO₂—C₆H₄ | N | |
| 47 | 4-Cl—C₆H₄ | 4-NO₂—C₆H₄ | N | |
| 48 | 4-Cl—C₆H₄ | 2-Cl-4-F—C₆H₃ | N | |
| 49 | 4-Cl—C₆H₄ | 2-Cl-4-F—C₆H₃ | CH | |
| 50 | 4-Cl—C₆H₄ | 4-NH₂—C₆H₄ | N | |
| 51 | 4-Cl—C₆H₄ | 3-NH₂—C₆H₄ | CH | |
| 52 | 4-Cl—C₆H₄ | 2-OCH₃—C₆H₄ | N | |
| 53 | 4-Cl—C₆H₄ | 4-OCH₃—C₆H₄ | N | |
| 54 | 4-Cl—C₆H₄ | cyclohexyl | N | |
| 55 | 4-Cl—C₆H₄ | cyclohexyl | CH | |
| 56 | 4-Cl—C₆H₄ | cyclohexenyl | N | |
| 57 | 4-Cl—C₆H₄ | cyclopentyl | N | |
| 58 | 2-Cl—C₆H₄ | phenyl | N | |
| 59 | 2-Cl—C₆H₄ | 2-Cl—C₆H₄ | N | |
| 60 | 2-Cl—C₆H₄ | 3-Cl—C₆H₄ | N | |
| 61 | 2-Cl—C₆H₄ | 4-Cl—C₆H₄ | N | |
| 62 | 2-Cl—C₆H₄ | 2,4-Cl₂—C₆H₃ | N | |
| 63 | 2-Cl—C₆H₄ | 2-F—C₆H₄ | N | |
| 64 | 2-Cl—C₆H₄ | 4-F—C₆H₄ | N | |
| 65 | 2-Cl—C₆H₄ | 2-Cl-4-F—C₆H₃ | N | |
| 66 | 2-Cl—C₆H₄ | 3-NO₂—C₆H₄ | N | |
| 67 | 2-Cl—C₆H₄ | 4-NO₂—C₆H₄ | N | |
| 68 | 2-Cl—C₆H₄ | 3-NH₂—C₆H₄ | N | |
| 69 | 2-Cl—C₆H₄ | 4-NH₂—C₆H₄ | N | |
| 70 | 2-Cl—C₆H₄ | 2-OCH₃—C₆H₄ | N | |
| 71 | 2-Cl—C₆H₄ | 4-OCH₃—C₆H₄ | N | |
| 72 | 2-Cl—C₆H₄ | cyclohexyl | N | |
| 73 | 2-Cl—C₆H₄ | cyclohexenyl | N | |
| 74 | 2-Cl—C₆H₄ | cyclopentyl | N | |
| 75 | 2-Cl—C₆H₄ | tert.-butyl | N | |
| 76 | 2-Cl—C₆H₄ | norbornyl | N | |

TABLE-continued

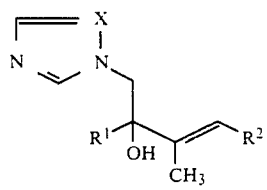

| Example | R₁ | R₂ | X | M.p./IR (°C.) |
|---|---|---|---|---|
| 77 | 2-Cl—C₆H₄ | iso-propyl | N | |
| 78 | 2-F—C₆H₄ | phenyl | N | |
| 79 | 2-F—C₆H₄ | 2-Cl—C₆H₄ | N | |
| 80 | 2-F—C₆H₄ | 3-Cl—C₆H₄ | N | |
| 81 | 2-F—C₆H₄ | 4-Cl—C₆H₄ | N | |
| 82 | 2-F—C₆H₄ | 2,4-Cl₂—C₆H₃ | N | |
| 83 | 2-F—C₆H₄ | 2-F—C₆H₄ | N | |
| 84 | 2-F—C₆H₄ | 4-F—C₆H₄ | N | |
| 85 | 2-F—C₆H₄ | 4-NO₂—C₆H₄ | N | |
| 86 | 2-F—C₆H₄ | 3-NH₂—C₆H₄ | N | |
| 87 | 2-F—C₆H₄ | 2-OCH₃—C₆H₄ | N | |
| 88 | 2-F—C₆H₄ | cyclohexyl | N | |
| 89 | 4-F—C₆H₄ | 2-Cl—C₆H₄ | N | 159–162 |
| 90 | 4-F—C₆H₄ | 2-Cl—C₆H₄ | CH | 140–142 |
| 91 | 4-F—C₆H₄ | 3-Cl—C₆H₄ | N | |
| 92 | 4-F—C₆H₄ | 4-Cl—C₆H₄ | N | |
| 93 | 4-F—C₆H₄ | 4-Cl—C₆H₄ | CH | |
| 94 | 4-F—C₆H₄ | 2,4-Cl₂—C₆H₃ | N | 174–176 |
| 95 | 4-F—C₆H₄ | 2,4-Cl₂—C₆H₃ | CH | 155–157 |
| 96 | 4-F—C₆H₄ | 2-F—C₆H₄ | N | 134–139 |
| 97 | 4-F—C₆H₄ | 2-F—C₆H₄ | CH | 121 |
| 98 | 4-F—C₆H₄ | 4-F—C₆H₄ | CH | |
| 99 | 4-F—C₆H₄ | 4-F—C₆H₄ | N | |
| 100 | 4-F—C₆H₄ | 4-NO₂—C₆H₄ | N | |
| 101 | 4-F—C₆H₄ | 3-NH₂—C₆H₄ | N | |
| 102 | 4-F—C₆H₄ | 2-OCH₃—C₆H₄ | N | |
| 103 | 4-F—C₆H₄ | cyclohexyl | N | |
| 104 | 2,4-Cl₂—C₆H₃ | phenyl | N | |
| 105 | 2,4-Cl₂—C₆H₃ | 2-Cl—C₆H₄ | N | |
| 106 | 2,4-Cl₂—C₆H₃ | 3-Cl—C₆H₄ | N | |
| 107 | 2,4-Cl₂—C₆H₃ | 4-Cl—C₆H₄ | N | |
| 108 | 2,4-Cl₂—C₆H₃ | 2,4-Cl₂—C₆H₃ | N | |
| 109 | 2,4-Cl₂—C₆H₃ | 2-F—C₆H₄ | N | |
| 110 | 2,4-Cl₂—C₆H₃ | 4-F—C₆H₄ | N | |
| 111 | 2,4-Cl₂—C₆H₃ | 4-NH₂—C₆H₄ | N | |
| 112 | 2,4-Cl₂—C₆H₃ | 2-OCH₃—C₆H₄ | N | |
| 113 | 2,4-Cl₂—C₆H₃ | cyclohexyl | N | |
| 114 | 2-OCH₃—C₆H₄ | 2-Cl—C₆H₄ | N | |
| 115 | 2-OCH₃—C₆H₄ | 4-Cl—C₆H₄ | N | |
| 116 | 2-OCH₃—C₆H₄ | 2-F—C₆H₄ | N | |
| 117 | 2-OCH₃—C₆H₄ | 4-F—C₆H₄ | N | |
| 118 | 4-OCH₃—C₆H₄ | 2-Cl—C₆H₄ | N | resin |
| 119 | 4-OCH₃—C₆H₄ | 4-Cl—C₆H₄ | N | |
| 120 | 4-OCH₃—C₆H₄ | 2-F—C₆H₄ | N | |
| 121 | 4-OCH₃—C₆H₄ | 4-F—C₆H₄ | N | |
| 122 | cyclohexyl | 2-Cl—C₆H₄ | N | |
| 123 | cyclohexyl | 4-Cl—C₆H₄ | N | |
| 124 | cyclohexyl | 2-F—C₆H₄ | N | |
| 125 | cyclohexyl | 4-F—C₆H₄ | N | |
| 126 | cyclohexyl | 2,4-Cl₂—C₆H₃ | N | |
| 127 | cyclohexyl | 4-F—C₆H₄ | CH | |
| 128 | cyclohexyl | cyclohexyl | N | |
| 129 | 4-F—C₆H₄ | 2-CF₃—C₆H₄ | N | 103–106 |
| 130 | 4-F—C₆H₄ | 2-CF₃—C₆H₄ | CH | 153 |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane, Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 7 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 34 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 34 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 39 is intimately mixed with 97 parts by weight of particulate kaolin. A dust is obtained containing 3% by weight of the active ingredient.

VII. 30 parts by weight of compound no. 89 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate, ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, 1-(1,2,4-triazol-1-ylmethyl)-1-(4-chlorophenyl)-3-(2-chlorophenyl)-prop-2-en-1-ol (A) disclosed in EP No. 52,424 was used.

USE EXAMPLE 1

Action on Pyrenophora teres

Barley seedlings of the "Igri" variety were sprayed to runoff at the two-leaf stage with aqueous suspensions containing (dry basis) 80 wt % of active ingredient and 20% of emulsifier. After 24 hours, the plants were inoculated with a spore suspension of the fungus Pyrenophora teres and placed for 48 hours in a high-humidity climatic cabinet at 18° C. The plants were then cultivated in the greenhouse at from 20° to 22° C. and a relative humidity of 70% for a further 5 days. The extent of the spread of the symptoms was then assessed.

The results show that active ingredients 1, 2, 7, 34, 39 and 89, when applied as a 0.05% spray liquor, have a better fungicidal action (90%) than the prior art active ingredient A used for comparison purposes (50%).

We claim:
1. Azolylmethylallyl alcohol of the formula I

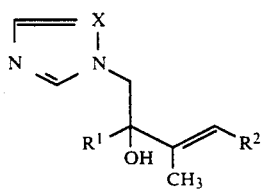

wherein $R^1$ is phenyl substituted by halogen; $R^2$ is phenyl substituted by halogen; X is N; and their plant-tolerated acid addition salts and metal complexes thereof.

2. Azolylmethylallyl alcohol of the formula I in claim 1, wherein $R_1$ is fluoro- or chloro-substituted phenyl.

3. A compound as set forth in claim 1, where $R^1$ is 4-chlorophenyl, $R^2$ is 2-chlorophenyl.

4. A compound as set forth in claim 1, where $R^1$ is 4-fluorophenyl, $R^2$ is 2-chlorophenyl.

5. A fungicidal composition containing an inert carrier and a fungicidally effective amount of an azolylmethylallyl alcohol of the formula I

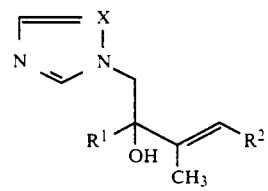

where $R^1$ is phenyl substituted by halogen; $R^2$ is phenyl substituted by halogen; X is N; or a plant-tolerated acid addition salt or metal complex thereof.

6. A process for combating fungi, wherein a fungicidally effective amount of an azolylmethylallyl alcohol of the formula I

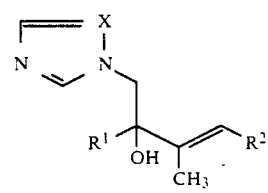

where $R^1$ is phenyl substituted by halogen; $R^2$ is phenyl substituted by halogen; X is N; or a plant-tolerated acid addition salt or metal complex thereof, is allowed to act on plant materials, areas, plants or seed threatened by fungus attack.

* * * * *

UNITED STATES PATENT AND TRADEMARK OFFICE
CERTIFICATE OF CORRECTION

PATENT NO. : 5,017,595
DATED : May 21, 1991
INVENTOR(S) : Rainer Seele et al

It is certified that error appears in the above-identified patent and that said Letters Patent is hereby corrected as shown below:

On the title page, please insert item [30] Foreign Application Priority Data:

--March 18, 1988  [DE] Fed. Rep. of Germany............... 3809069--.

Signed and Sealed this

Sixteenth Day of March, 1993

Attest:

STEPHEN G. KUNIN

*Attesting Officer*     *Acting Commissioner of Patents and Trademarks*